(12) United States Patent
Keller

(10) Patent No.: US 6,500,207 B1
(45) Date of Patent: Dec. 31, 2002

(54) JOINT ENDOPROSTHESIS

(75) Inventor: Arnold Keller, Kayhude (DE)

(73) Assignee: Waldemar Link GmbH & Co., Hamburg (DE)

( * ) Notice: Subject to any disclaimer, the term of this patent is extended or adjusted under 35 U.S.C. 154(b) by 48 days.

(21) Appl. No.: 09/640,691

(22) Filed: Aug. 18, 2000

(30) Foreign Application Priority Data

Sep. 24, 1999 (EP) .............................................. 99118860

(51) Int. Cl.[7] .................................................. A61F 2/32
(52) U.S. Cl. ................................ 623/20.15; 623/22.42; 623/23.44
(58) Field of Search ............................ 623/16.11, 18.11, 623/20.14, 20.15, 20.25, 20.34, 20.36, 22.11, 22.4, 22.41, 22.42, 22.43, 22.45, 23.18, 23.44

(56) References Cited

U.S. PATENT DOCUMENTS 4,790,854 A * 12/1988 Harder et al. ............. 623/20.15
5,147,406 A *  9/1992 Houston et al. ......... 623/20.15

* cited by examiner

*Primary Examiner*—David J. Isabella
(74) *Attorney, Agent, or Firm*—Morrison & Foerster LLP

(57) ABSTRACT

Joint endoprosthesis with an anchoring part (3) and a cone connection (4) between a joint part (1) and the anchoring part (3). According to the invention, the cone connection is provided with an anti-rotation arrangement (13, 14). It can also be equipped with a securing screw (8).

8 Claims, 2 Drawing Sheets

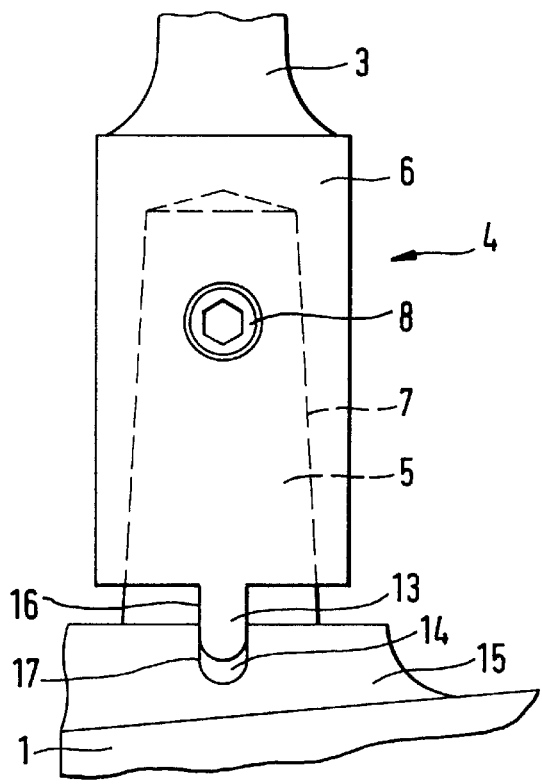
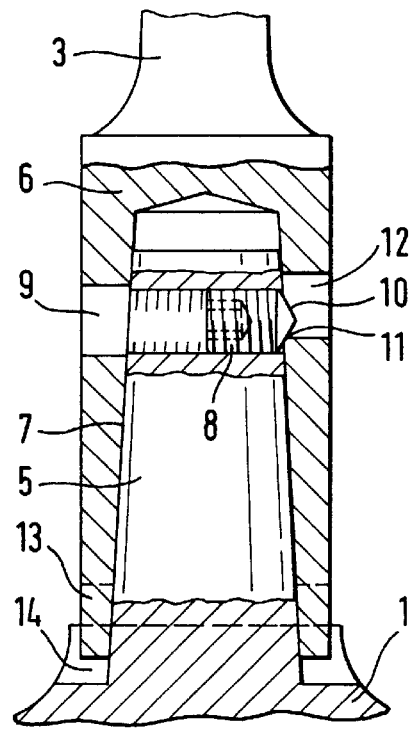
Fig. 2                    Fig. 3

JOINT ENDOPROSTHESIS

In addition to those components which serve to simulate the joint function, joint endoprostheses have parts for anchoring them to the bone. If different anchoring parts are kept available for one prosthesis, the anchoring part chosen in each case is connected to an associated joint component via a connection device. For this purpose, cone connections have proven themselves which consist of a cone stub and of a cone sleeve which are designed with the same slight cone angle, for example of 5°, and which generally stick sufficiently firmly in each other as soon as they have been joined together under the effect of an impact. Unless considerable forces arise acting in the direction of separation of the connection, further securing means are not necessary. This applies, for example, when fastening hip-joint heads to the associated stem parts (U.S. Pat. No. 5,336,268). If substantial releasing forces have to be taken into account, the cone connection is provided with a securing screw (EP-A 474015). For example, a grub screw can be included in the cone stub, the conical tip of which screw is screwed into engagement with a bore, eccentric thereto, of the cone sleeve (EP-A 474015, FIG. 3).

It is also known (U.S. Pat. No. 5,405,403) for a cone connection to be provided with an anti-rotation arrangement in order to prevent relative turning between the cone surfaces, as this could lead to corrosion.

A securing screw not only prevents a translatory movement of the coupled parts in the axial direction, but also prevents a rotational movement. Thus, a securing screw traditionally also performs the functions of an anti-rotation arrangement.

The invention has taken recognition of the fact that considerable advantages can be achieved by combining a securing screw with an anti-rotation arrangement, if the securing screw interacts with a bore, eccentric thereto, via a conical tip. When such a securing screw is used without an anti-rotation arrangement, as in the prior art, it is not possible to guarantee that the conical tip of the securing screw will interact precisely with that point of the bore edge which lies nearest to the thicker end of the cone connection during assembly. It is only then, in fact, that exact anti-rotation by the securing screw is obtained. However, if the contact point lies slightly to the side of this ideal point of interaction, microrotation movements are possible. The combination according to the invention thus ensures, however, that a certain contact point between the conical tip, the securing screw and the associated bore is fixed. This not only prevents the said micro movements, but also prevents the securing screw from becoming worn, from twisting and possibly from wholly or partially losing its securing function as a result of relative movements with respect to the bore edge which interacts with it.

This is of particular importance when the securing screw is provided with a predetermined break point (EP-A 915686=WO 9804215). The anti-rotation arrangement thus has the effect that the securing screw can fulfil its function in the desired manner.

To provide this anti-rotation arrangement, projections and recesses are expediently formed on the two coupling parts and interact with each other via axially parallel flanks. For example, at least one stub can project in an axially parallel manner from the edge of the cone sleeve and engage in a correspondingly shaped groove which is provided at the base of the cone stub. Conversely, it is also possible for the edge of the cone sleeve to be provided with at least one indentation into which a transverse pin provided on the cone stub engages.

The invention is explained in greater detail below with reference to the drawing which presents advantageous illustrative embodiments and in which:

FIGS. 2 and 3 show a side view and a sectional view of the cone connection.

Figure 1:
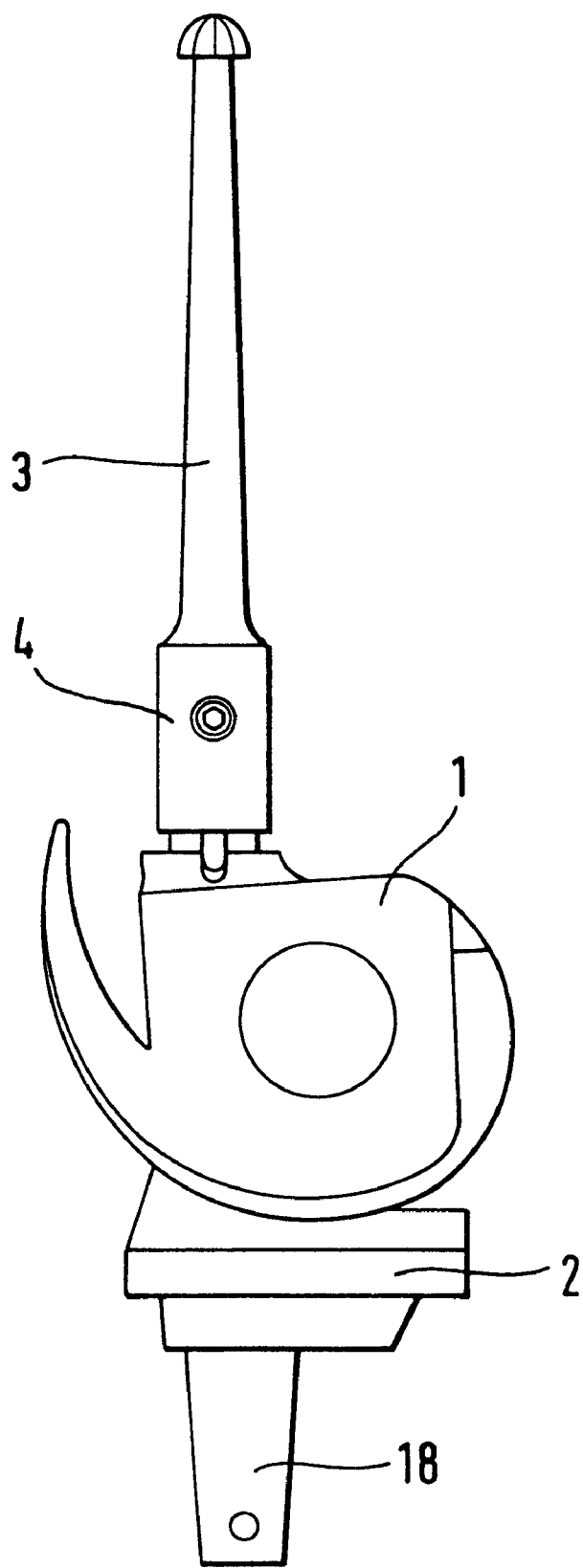
FIG. 1 shows the side view of a knee prosthesis.

The knee prosthesis shown in FIG. 1 has a femoral component 1 and a tibial component 2. The femoral component is shown connected to a stem 3, which is to be anchored in the cavity of the femoral bone. It is connected to the femoral component 1 via a cone connection 4. The tibial component 2 is likewise to be connected to an anchoring part (not shown) and for this purpose has, as part of a cone connection, a cone stub 5.

The cone connection consists of a cone stub 5 and of a cone sleeve 6 which are in mutual contact over a large surface area via surfaces 7 of identical conicity. The cone angle of these surfaces (angle between diametrically opposite envelope lines) is of the order of 5°, for example. It is dimensioned in such a way that the connection parts 5 and 6, having been joined together with force (for example by means of an impact), can only be separated again by considerable force and, in addition, can only be turned relative to each other counter to considerable frictional resistance. In some cases the strength of the connection may be put in doubt, namely if they have not been joined together sufficiently strongly upon implantation or if they have been loosened by an abnormally high release force during use. In this example, therefore, the connection stub 5 is provided with a grub screw 8 whose hexagonal head is accessible via a bore 9 on one side of the cone sleeve 6 and whose conical tip 10 interacts with the edge 11 of a bore 12 on the other side of the cone sleeve 6.

In order to free the screw 8 from loading by rotational forces, or, in the case of the absence of the screw 8, to ensure rotational securing of the connection, the anti-rotation arrangement according to the invention is provided which consists of two axially parallel stubs 13 on the edge of the cone sleeve 6 and corresponding grooves 14 in the collar 15 from which the cone stub 5 projects. The stubs 13 and the grooves 14 are in each case delimited by a pair of parallel flanks 16 and 17, respectively, the width of the groove 14 being no greater, or scarcely greater, than the width of the stubs 13.

Two anti-rotation arrangements 13, 14 lying approximately opposite each other are expediently provided.

The bores 9, 12 of the screw connection are not flush with each other. It must therefore be ensured that the cone sleeve 6 is applied on the stub 5 in a defined position of rotation in which the screw tip 10 interacts correctly with the bore 12. This can be ensured by the anti-rotation arrangement or arrangements being provided in such a way that this defined position of rotation arises. This is necessarily the case if only one anti-rotation arrangement 13, 14 is used, or if two anti-rotation arrangements are not positioned exactly diametrically opposite each other.

The anchoring part does not have to be a bone stem; it can also be the rod which, in the case of a total prosthesis of a bone section enclosed by two joints, connects a component of one joint to a component of the other joint.

What is claimed is:

1. A joint endoprosthesis, comprising an anchoring part and a cone connection comprising a cone sleeve and a cone stub, the cone connection being formed between a joint part and the anchoring part, wherein the cone connection comprises a securing screw having a conical tip configured to interact with an edge of a bore in the cone sleeve which is eccentric to the securing screw and a first anti-rotation means for securing the cone stub against rotation relative to the cone sleeve.

2. The joint endoprosthesis according to claim 1, wherein the first anti-rotation means comprises one part having a projection formed thereon and another part having a recess formed therein, the projection and the recess interacting with each other through respective axially parallel flanks on the projection and in the recess.

3. The joint endoprosthesis according to claim 2, wherein the first anti-rotation means further comprises at least one stub projecting from an edge of the cone sleeve and at least one groove corresponding to the at least one stub provided at a base portion of the cone stub.

4. The joint endoprosthesis according to claim 2, wherein the first anti-rotation means further comprises at least one indentation formed in an edge of the cone sleeve and at least one transverse pin corresponding to the at least one indentation provided on the cone stub.

5. The joint endoprosthesis according to claim 1, 2, 3 or 4, wherein the securing screw has a predetermined break point.

6. The joint endoprosthesis according to claim 3, wherein the groove has a width not substantially greater than the width of its corresponding stub projecting from an edge of the cone sleeve.

7. The joint endoprosthesis according to claim 5, further comprising a second anti-rotation means for securing the cone stub against rotation relative to the cone sleeve.

8. The joint endoprosthesis according to claim 7, wherein the second anti-rotation means is not positioned on the joint endoprosthesis exactly diametrically opposite the first anti-rotation means.

* * * * *

UNITED STATES PATENT AND TRADEMARK OFFICE
CERTIFICATE OF CORRECTION

PATENT NO. : 6,500,207 B1
DATED : December 31, 2002
INVENTOR(S) : Arnold Keller

It is certified that error appears in the above-identified patent and that said Letters Patent is hereby corrected as shown below:

<u>Title page,</u>
Item [56], References Cited, U.S. PATENT DOCUMENTS, please add:
-- 5,563,764 A   8/1997   Murphy
   5,405,403 A   4/1995   Mikhail --.
FOREIGN PATENT DOCUMENTS, please add:
-- 98/04215    2/1998    PCT
   2 673 832   9/1992    Europe
   0 376 658   7/1990    Europe
   0 339 530   11/1989   Europe --.

Signed and Sealed this

First Day of April, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,500,207 B1
DATED : December 31, 2002
INVENTOR(S) : Arnold Keller

It is certified that error appears in the above-identified patent and that said Letters Patent is hereby corrected as shown below:

<u>Title page,</u>
Item [56], References Cited, U.S. PATENT DOCUMENTS, please add:
-- 5,653,764 A    8/1997     Murphy
    5,405,403 A    4/1995     Mikhail --.
FOREIGN PATENT DOCUMENTS, please add:
-- 98/04215     2/1998     PCT
   2 673 832     9/1992     Europe
   0 376 658     7/1990     Europe
   0 339 530    11/1989     Europe --.

This certificate supersedes Certificate of Correction issued April 1, 2003

Signed and Sealed this

Tenth Day of June, 2003

JAMES E. ROGAN
*Director of the United States Patent and Trademark Office*